US008121796B2

(12) United States Patent
Hakki

(10) Patent No.: US 8,121,796 B2
(45) Date of Patent: Feb. 21, 2012

(54) APPARATUS AND METHOD FOR IDENTIFYING THE ORIGINAL FEMOROTIBIAL JOINT LOCATION IN A REVISION KNEE REPLACEMENT

(76) Inventor: Sam Hakki, Bay Pines, FL (US)

(\*) Notice: Subject to any disclaimer, the term of this patent is extended or adjusted under 35 U.S.C. 154(b) by 649 days.

(21) Appl. No.: 12/284,259

(22) Filed: Sep. 19, 2008

(65) Prior Publication Data

US 2009/0125243 A1 May 14, 2009

Related U.S. Application Data

(60) Provisional application No. 60/994,429, filed on Sep. 19, 2007.

(51) Int. Cl.
*G01N 33/48* (2006.01)
*A61M 35/00* (2006.01)
*A61B 17/58* (2006.01)
*A61F 2/38* (2006.01)

(52) U.S. Cl. .......... 702/19; 604/293; 606/99; 623/20.14

(58) Field of Classification Search .................... 702/19, 702/33–36, 81, 84–85, 94–95, 97, 127, 150–153, 702/155, 158, 166, 179, 182–183, 189; 604/11, 604/14, 19, 27–28, 293; 606/13–14, 53, 606/60, 99, 102, 281; 623/11.11, 13.12, 623/16.11, 20.14, 20.18–20.19, 20.2, 20.21–20.22, 623/20.32–20.36, 27, 39, 53
See application file for complete search history.

(56) References Cited

OTHER PUBLICATIONS

Zhao et al., Predicting Knee Replacement Damage in a Simulator Machine Using a Computational Model with a Consistent Wear Factor, Nov. 30, 2006, Department of Mechanical & Aerospace Engineering, University of Florida, 37 pp.*

* cited by examiner

*Primary Examiner* — Michael Nghiem
*Assistant Examiner* — Toan Le
(74) *Attorney, Agent, or Firm* — Frijouf, Rust & Pyle P.A.

(57) ABSTRACT

An apparatus and method is disclosed of identifying the original femorotibial joint location in a revision knee replacement of a patient. The invention includes selecting a first reference point (H) relative to the femoral head of the patient. A second reference point (A) is selected relative to the adductor tubical of the femur of the patient. The femorotibial joint location (J) is calculated through a relationship between the first reference point (H) and the second reference point (A) of the patient. The method and apparatus defines a femur reference plane to assist in establishing the correct rotation of the femur in a revision knee replacement of a patient.

15 Claims, 5 Drawing Sheets

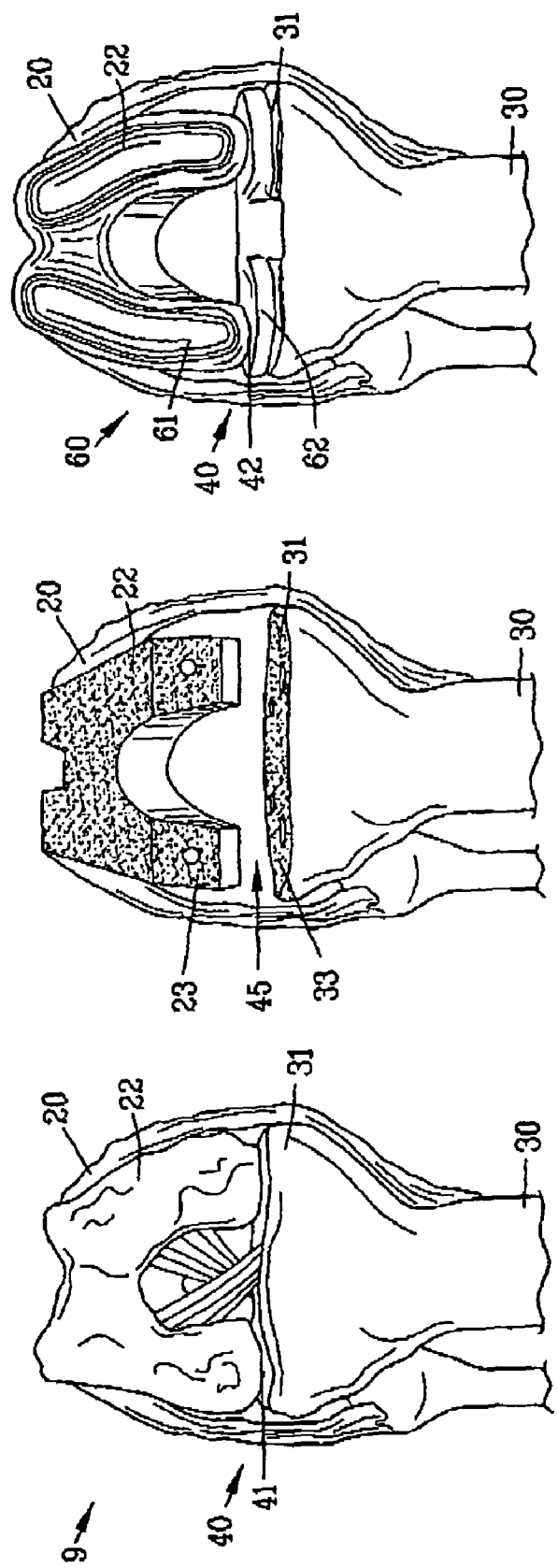

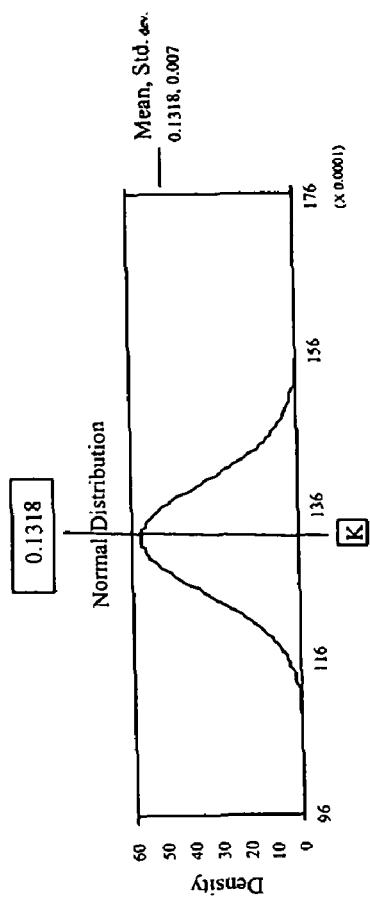
$$\frac{J-A}{H-A} = K$$
FIG. 7
FIG. 8
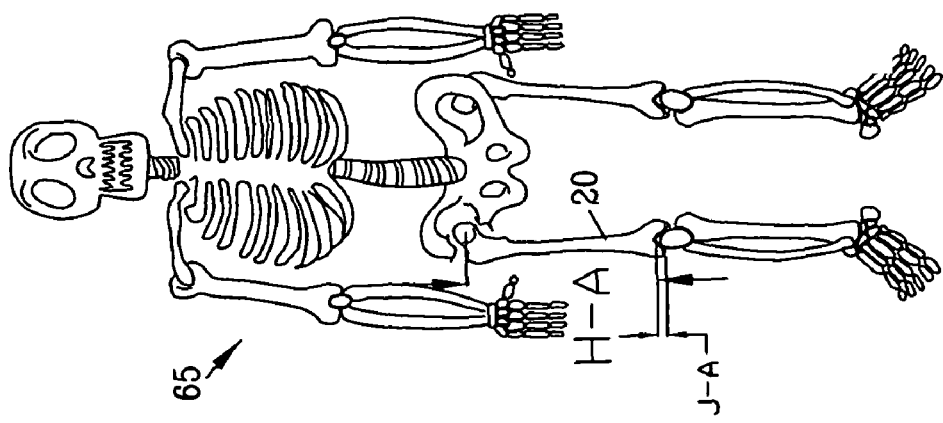
FIG. 6

APPARATUS AND METHOD FOR IDENTIFYING THE ORIGINAL FEMOROTIBIAL JOINT LOCATION IN A REVISION KNEE REPLACEMENT

CROSS-REFERENCE TO RELATED APPLICATIONS

This application claims benefit of U.S. Patent Provisional application No. 60/994,429 filed Sep. 19, 2007. All subject matter set forth in provisional application Ser. No. 60/994,429 is hereby incorporated by reference into the present application as if fully set forth herein.

BACKGROUND OF THE INVENTION

1. Field of the Invention

This invention relates to surgery and more particularly to an apparatus and a method for identifying the original femorotibial joint location in a revision knee replacement.

2. Background of the Invention

The knee joint is made of a thigh bone (femur), a leg bone (tibia) and a knee cap (patella). The femur and the tibia are coupled at a femorotibial joint defined by a femorotibial joint plane.

A total knee arthroplasty or a total knee replacement is a surgical procedure wherein worn, diseased, or damaged surfaces of the knee joint are removed and replaced with artificial surfaces. When a patient has a total knee replacement, the distal end of the femur is severed and a femur prosthesis is implanted to the severed distal end of the femur. In a similar manner, the proximal end of the tibia is severed and a tibia prosthesis is attached to the severed proximal end of the tibia.

Typically, the femur prosthesis has a metallic surface whereas the tibia prosthesis has a plastic surface. The femur prosthesis and the tibia prosthesis provide a metal to plastic surfaces for articulating the knee joint of the patient at the femorotibial joint plane. In most cases the undersurface of the patella is also replaced with a plastic surface to articulate with the femoral surface at a junction is called the patellofemoral joint.

Total knee replacements appear to have an 80% to 90% survival rate for the designed useful life of twenty years. Approximately 10% to 20% of total knee replacements involve complications requiring the removal of the original prosthesis and the re-implantation of a new prosthesis. In addition, many of the successful total knee replacements must be replace after the expiration of the designed useful life of the prosthesis.

The re-implant of the new prostheses is referred to as a revision knee replacement. In the revision knee replacement, the femur prosthesis and the tibia prosthesis are removed and the new prostheses are implanted into the patient.

A revision surgery is more complex than the original knee replacement surgery. The revision surgery is more complex due to the difficulty of removing the original prosthesis and the quality and quantity of bone left behind after removal of the original prosthesis.

Among the most significant problems of a revision knee replacement surgery is the loss of the original femorotibial joint location. Since the distal end of the femur and the proximal end of the tibia were severed in the original nee replacement surgery, a void is present between the distal end of the femur and the proximal end of the tibia. The original femorotibial joint location as well as the orientation of the original rotation of the femur is not readily apparent to the surgeon.

If the second prosthesis is not properly located in the revision knee replacement surgery, the femur and the tibia will not be located and orientated properly relative to the collateral ligaments. The lack of a properly located and orientated femur and tibia with the collateral ligaments will restrict the range of motion of the knee joint for the patient.

Therefore, it is an object of this invention to provide an improved method and apparatus of identifying the original femorotibial joint location in a revision knee replacement of a patient.

Another object of this invention is to provide an improved method and apparatus for defining a femur reference plane to assist in establishing the correct rotation of the femur in a revision knee replacement of a patient.

The foregoing has outlined some of the more pertinent objects of the present invention. These objects should be construed as being merely illustrative of some of the more prominent features and applications of the invention. Many other beneficial results can be obtained by modifying the invention with in the scope of the invention. Accordingly other objects in a full understanding of the invention may be had by referring to the summary of the invention and the detailed description describing the preferred embodiment of the invention.

SUMMARY OF THE INVENTION

The present invention is defined by the appended claims with specific embodiments being shown in the attached drawings. For the purpose of summarizing the invention, the invention relates to an improved method of identifying the original femorotibial joint location in a revision knee replacement of a patient. The method comprises selecting a first reference point (H) relative to the femoral head of the patient. A second reference point (A) is selected relative to the adductor tubical of the femur of the patient. The distance is determined between the first reference point (H) and the second reference point (A). The original femorotibial joint location (J) of the patient is calculated through a mathematical relationship between the first reference point (H) and the second reference point (A).

In a more specific embodiment of the invention, the step of locating the original femorotibial joint location (J) includes locating the original femorotibial joint location (J) through the mathematical relationship of the distance (J-A) divided by the distance (H-A) is equal to a constant.

In another embodiment of the invention, the invention is incorporated into a method of identifying the rotation of the femur in a revision knee replacement of a patient. The method comprises the step of selecting a first reference point (H) relative to the femoral head of the patient. A second reference point (A) is selected a relative to the adductor tubical of the femur of the patient. A third reference point (N) is selected relative to a center of a notch of the distal end of the femur of the patient. A femur reference plane is calculated to extend through the first reference point (H), the second reference point (A) and the third reference point (N). The femur reference plane assists in establishing the correct rotation of the femur in a revision knee replacement of the patient.

In still another embodiment of the invention, the invention is incorporated into an apparatus for identifying the original femorotibial joint location in a revision knee replacement of a patient. The apparatus comprises a sensor for sensing a spatial relationship with the between the first reference point (H) and second reference point (A) of the patient. A calculator determines the original femorotibial joint location (J) of the patient through a mathematical relationship of the first reference point (H) and the second reference point (A). An indicator indicates the position of the original femorotibial joint location of the patient.

In still a further embodiment of the invention, the invention is incorporated into an apparatus for identifying the original rotation of the femur. The apparatus comprises a calculator for providing a femur reference plane extending through the first reference point (H), the second reference point (A) and the third reference point (N). An indicator indicates the position of the femur reference plane to assist in establishing the correct rotation of the femur in a revision knee replacement of the patient.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be made to the following detailed description taken in connection with the accompanying drawings in which:

FIG. 3 is view similar to FIG. 2 illustrating a damaged femorotibial joint;

FIG. 4 is view similar to FIG. 3 illustrating cut femur and tibia bones in preparation for a total knee replacement;

FIG. 5 is view similar to FIG. 4 illustrating a prostheses implanted between the cut femur and tibia bones;

FIG. 6 is a front view of a skeletal structure illustrating proportions within the femur bone;

FIG. 7 is a mathematical relationship of regarding proportions within the femur bone of FIG. 6;

FIG. 8 is a graph illustrating the distribution of proportions within the femur bone;

Similar reference characters refer to similar parts throughout the several Figures of the drawings.

DETAILED DISCUSSION

Figure 1:
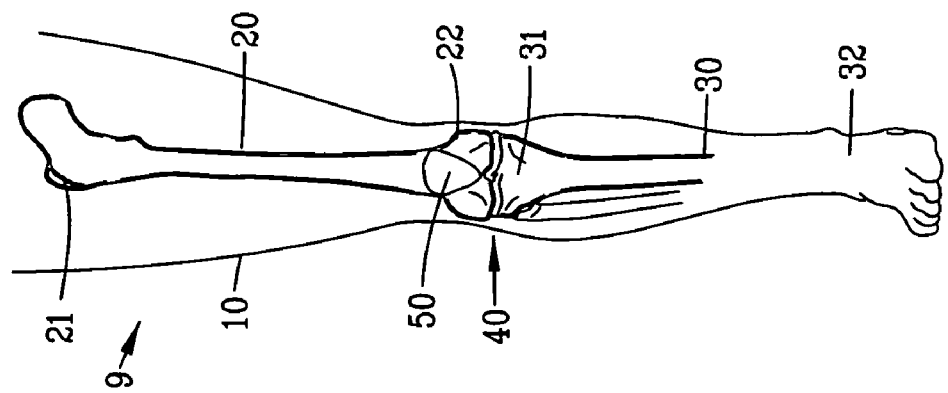
FIG. 1 is a front view of a leg partially in section illustrating the femur and the tibia bones of a patient.

FIG. 1 is a front view of a right leg 10 partially in section of a patient 11. A femur bone 20 extends from a proximal end 21 to a distal end 22. A tibia 30 extends from a proximal end 31 to a distal end 32. The distal end 22 of the femur is located adjacent to the proximal end 31 of the tibia forming a femorotibial joint 40. A patella 50 the shown located adjacent to the distal end 22 of the femur 20.

Figure 2:
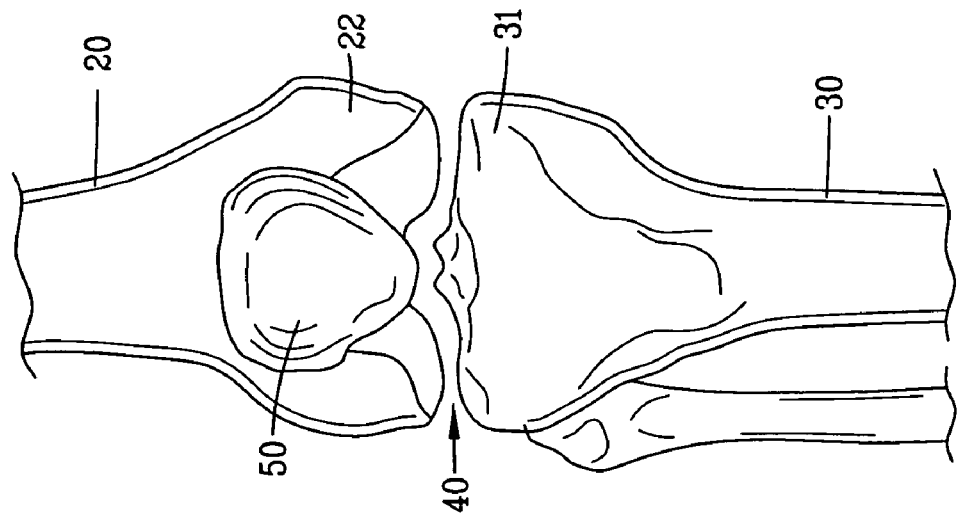
FIG. 2 is an enlarged view of a femorotibial joint portion of FIG. 1.

FIG. 2 is an enlarged view of a femorotibial joint 40 portion of FIG. 1. The femorotibial joint 40 provides articulation between the femur 20 and the tibia 30. It should be appreciated that by those skilled in the medical art that the drawings have been simplified for the sake of clarity in setting forth the present invention.

FIG. 3 is view similar to FIG. 2 illustrating a damaged femorotibial joint 40. In many cases, the surface of the distal end 22 of the femur 20 and/or the surface of the proximal end 31 of the tibia 30 are damaged by injury, disease and the like. The damage to the distal end 22 to the femur and/or the proximal end 31 of the tibia 30 results in a painful articulation between the femur 20 and the tibia 30 for the patient 11. The location of the original femorotibial joint 40 is shown as 41.

FIG. 4 is view similar to FIG. 3 illustrating a step in a total knee replacement surgery operation. The details of a total knee replacement surgery should be well known by those skilled in the medical art. The distal end 22 of the femur 20 has been severed to define a severed distal and 23. In a similar manner, the proximal end 31 of the tibia 30 has been severed to define a severed proximal end 33. The severing of the distal end 22 of the femur 20 the proximal end 31 of the tibia 30 remove the damage surface of the distal end 22 of the femur 20 and/or the surface of the proximal end 31 of the tibia 30.

The severing of the distal end 22 of the femur 20 the proximal end 31 of the tibia 30 results in a gap 45 between the distal end 22 of the femur 20 the proximal end 31 of the tibia 30. The gap 45 between the distal end 22 of the femur 20 the proximal end 31 of the tibia 30 destroys the location of the original femorotibial joint 41.

Prior to severing the distal end 22 of the femur 20 and the proximal and 31 of the tibia 30, the location of the original femorotibial joint 41 is recorded in order to preserve the proper location of the femorotibial joint 41.

FIG. 5 is view similar to FIG. 4 illustrating prostheses 60 implanted between the severed distal end 23 of the femur 20 and the severed proximal end 31 of the tibia 30. A femur prosthesis 61 is implanted to the severed distal end 22 of the femur 20. A tibia prosthesis 62 is implanted to the severed proximal end 31 of the tibia 30. The femur prosthesis 61 and the tibia prosthesis 62 establish a first implant femorotibial joint 42. The Under proper conditions, the first implant femorotibial joint 42, is located at the position of the original femorotibial joint 41.

The surgical procedure for removing the original prostheses 60 shown in FIG. 5 and re-implantation new prostheses (not shown) is referred to as a revision knee replacement. Upon the removal of the original prostheses 60 shown in FIG. 5, the surgeon is faced with the gap 45 between the distal end 22 of the femur 20 the proximal end 31 of the tibia 30 and the loss of the original femorotibial joint 41 as shown in FIG. 4.

Identification of the original femorotibial joint 41 in a revision knee replacement is very difficult. Many surgeons relied on relation to the fibula head which proved recently to be unreliable. Other surgeons relied on first implant femorotibial joint 42 shown in FIG. 5 established by previous knee replacement surgeons. In many cases the first implant femorotibial joint 42 also proved to be unreliable.

FIG. 6 is a front view of a skeleton 65 illustrating proportions within the skeletal structure. Statistics regarding the proportions within the skeletal structure may be found in the Stat Advisor. The details of the femur 20 are shown with reference to FIGS. 9 and 10. A first reference point (H) is selected relative to the femoral head 70 of the patient 11. Preferably, the first reference point (H) is the center 72 of the femoral head 70 of the patient 11.

A second reference point (A) is selected relative to the adductor tubical 80 of the femur 20 of the patient 11. Preferably, the second reference point (A) is the adductor tubical 80 of the patient 11. The distance between the first reference point (H) and the second reference point (A) is H-A. The original femorotibial joint location (J) 41 may be calculated through a relationship between the first reference point (H) and the second reference point (A).

FIG. 7 is a mathematical relationship of regarding proportions within the femur bone 20 of FIG. 6. The location of the original femorotibial joint location (J) 41 may be calculated through the relationship of the distance (J-A) divided by the distance (H-A) is equal to a constant.

$$\frac{\text{distance}(J-A)}{\text{distance}(H-A).} = K = \text{constant}$$

The mathematical relationship of the skeletal structure is established by the following correlation analysis.

r K and Height

The output from the Stat Advisor shows the results of fitting a linear model to describe the relationship between Height and K. The equation of the fitted model is:

Height=64.0887+41.3957*K

Since the P-value in the ANOVA table is greater or equal to 0.10, there is not a statistically significant relationship between Height and K at the 90% or higher confidence level.

The R-Squared statistic indicates that the model as fitted explains 0.815508% of the variability in Height. The correlation coefficient equals 0.0903055, indicating a relatively weak "NO" relationship between the variables. The standard error of the estimate shows the standard deviation of the residuals to be 3.23187. This value can be used to construct prediction limits for new observations by selecting the Forecasts option from the text menu.

r K and Race

The output from the Stat Advisor shows the results of fitting a linear model to describe the relationship between Race and K. The equation of the fitted model is:

Race=1.16337−0.273804*K

Since the P-value in the ANOVA table is greater or equal to 0.10, there is not a statistically significant relationship between Race and K at the 90% or higher confidence level.

The R-Squared statistic indicates that the model as fitted explains 0.00245564% of the variability in Race. The correlation coefficient equals −0.00495544, indicating a relatively weak "NO" relationship between the variables. The standard error of the estimate shows the standard deviation of the residuals to be 0.39115. This value can be used to construct prediction limits for new observations by selecting the Forecasts option from the text menu.

r K and H-A

The output from the Stat Advisor shows the results of fitting a linear model to describe the relationship between H A and K. The equation of the fitted model is:

H-A=53.0451−28.811*K

Since the P-value in the ANOVA table is greater or equal to 0.10, there is not a statistically significant relationship between H A and K at the 90% or higher confidence level.

The R-Squared statistic indicates that the model as fitted explains 0.406662% of the variability in H-A. The correlation coefficient equals −0.06377, indicating a relatively weak "NO" relationship between the variables. The standard error of the estimate shows the standard deviation of the residuals to be 3.19189. This value can be used to construct prediction limits for new observations by selecting the Forecasts option from the text menu.

r K and J-A "Autocorrelation"

The output from the Stat Advisor shows the results of fitting a linear model to describe the relationship between J A and K. The equation of the fitted model is:

JA=0.447728+45.8724*K

Since the P-value in the ANOVA table is less than 0.01, there is a statistically significant relationship between J A and K at the 99% confidence level.

The R-Squared statistic indicates that the model as fitted explains 37.3411% of the variability in J A. The correlation coefficient equals 0.611073, indicating a moderately strong "autocorrelation" relationship between the variables. The standard error of the estimate shows the standard deviation of the residuals to be 0.420669. This value can be used to construct prediction limits for new observations by selecting the Forecasts option from the text menu.

r K and Weight

The output from the Stat Advisor shows the results of fitting a linear model to describe the relationship between Weight and K. The equation of the fitted model is:

Weight=54.9946+1168.87*K

Since the P-value in the ANOVA table is less than 0.10, there is a statistically significant relationship between Weight and K at the 90% confidence level.

The R-Squared statistic indicates that the model as fitted explains 5.70836% of the variability in Weight. The correlation coefficient equals 0.238922, indicating a relatively weak relationship between the variables. The standard error of the estimate shows the standard deviation of the residuals to be 33.6308. This value can be used to construct prediction limits for new observations by selecting the forecasts option from the text menu.

r K and Gender

The output from the Stat Advisor shows the results of fitting a linear model to describe the relationship between Gender n and K. The equation of the fitted model is:

Gender=0.277747+5.06537*K

Since the P-value in the ANOVA table is greater or equal to 0.10, there is not a statistically significant relationship between Gender and K at the 90% or higher confidence level.

The R-Squared statistic indicates that the model as fitted explains 2.4028% of the variability in Gender n. The correlation coefficient equals 0.15501, indicating a relatively weak relationship between the variables. The standard error of the estimate shows the standard deviation of the residuals to be 0.22854. This value can be used to construct prediction limits for new observations by selecting the forecasts option from the text menu.

The following is a comparison analysis of age, height and weight.

Age

This option runs a t-test to compare the means of the two samples. It also constructs confidence intervals for each mean and for the difference between the means. Of particular interest is the confidence interval for the difference between the means, which extends from −10.4041 to 9.5291. Since the interval contains the value 0.0, there is not a statistically significant difference between the means of the two samples at the 95.0% confidence level. The t-tests can also be used to arrive at the same conclusion. P-values below 0.05 indicate significant differences between the two means.

NOTE: the interval used above assumes that the variances of the two samples are equal. This was determined by running an F-test to compare the standard deviations of the two samples. You can see the results of that test by selecting Comparison of Standard Deviations from the Tabular Options menu.

Height

This option runs a t-test to compare the means of the two samples. It also constructs confidence intervals for each mean and for the difference between the means. Of particular interest is the confidence interval for the difference between the means, which extends from −5.24415 to 0.465234. Since the interval contains the value 0.0, there is not a statistically significant difference between the means of the two samples at the 95.0% confidence level. The t-tests can also be used to arrive at the same conclusion. P-values below 0.05 indicate significant differences between the two means. (*Statistical significance, not assuming equal variances.)

NOTE: the interval used above does not assume that the variances of the two samples are equal. This was determined by running an F-test to compare the standard deviations of the two samples. You can see the results of that test by selecting Comparison of Standard Deviations from the Tabular Options menu.

Weight

This option runs a t-test to compare the means of the two samples. It also constructs confidence intervals for each mean and for the difference between the means. Of particular interest is the confidence interval for the difference between the means, which extends from −54.3857 to 4.08637. Since the interval contains the value 0.0, there is not a statistically significant difference between the means of the two samples at the 95.0% confidence level. The t-tests can also be used to arrive at the same conclusion. P-values below 0.05 indicate significant differences between the two means. (*Statistical significance, not assuming equal variances.)

NOTE: the interval used above assumes that the variances of the two samples are equal. This was determined by running an F-test to compare the standard deviations of the two samples. You can see the results of that test by selecting Comparison of Standard Deviations from the Tabular Options menu.

J-A

This option runs a t-test to compare the means of the two samples. It also constructs confidence intervals for each mean and for the difference between the means. Of particular interest is the confidence interval for the difference between the means, which extends from −0.800197 to 0.101558. Since the interval contains the value 0.0, there is not a statistically significant difference between the means of the two samples at the 95.0% confidence level. The t-tests can also be used to arrive at the same conclusion. P-values below 0.05 indicate significant differences between the two means. (*Statistical significance, not assuming equal variances.)

NOTE: the interval used above assumes that the variances of the two samples are equal. This was determined by running an F-test to compare the standard deviations of the two samples. You can see the results of that test by selecting Comparison of Standard Deviations from the Tabular Options menu.

H-A

This option runs a t-test to compare the means of the two samples. It also constructs confidence intervals for each mean and for the difference between the means. Of particular interest is the confidence interval for the difference between the means, which extends from −4.25549 to 1.231. Since the interval contains the value 0.0, there is not a statistically significant difference between the means of the two samples at the 95.0% confidence level. The t-tests can also be used to arrive at the same conclusion. P-values below 0.05 indicate significant differences between the two means.

NOTE: the interval used above assumes that the variances of the two samples are equal. This was determined by running an F-test to compare the standard deviations of the two samples. You can see the results of that test by selecting Comparison of Standard Deviations from the Tabular Options menu.

K

This option runs a t-test to compare the means of the two samples. It also constructs confidence intervals for each mean and for the difference between the means. Of particular interest is the confidence interval for the difference between the means, which extends from −0.00888237 to 0.00330414. Since the interval contains the value 0.0, there is not a statistically significant difference between the means of the two samples at the 95.0% confidence level. The t-tests can also be used to arrive at the same conclusion. P-values below 0.05 indicate significant differences between the two means.

NOTE: the interval used above assumes that the variances of the two samples are equal. This was determined by running an F-test to compare the standard deviations of the two samples. You can see the results of that test by selecting Comparison of Standard Deviations from the Tabular Options menu.

FIG. 8 is a graph illustrating the distribution of proportions within the femur bone 20. The graph yields the following valve for the constant K/

$$\frac{\text{distance}(J\text{-}A)}{\text{distance}(H\text{-}A).} = 0.13$$

The following is a summary of the above analysis of the proportions within the skeletal structure of FIG. 6.

| | |
|---|---|
| Age | 70 |
| Gender | 95% male |
| | 5% female |

| | |
|---|---|
| Race | 89% Caucasian |
| | 9% African American |
| | 2% Hispanic |
| Height | 69.5 ± 3.2 |
| Weight | 209.1 ± 34.3 |
| H-A | 49.247 ± 0.526 |
| K | 0.1318 ± 0.007 |

Figure 9:
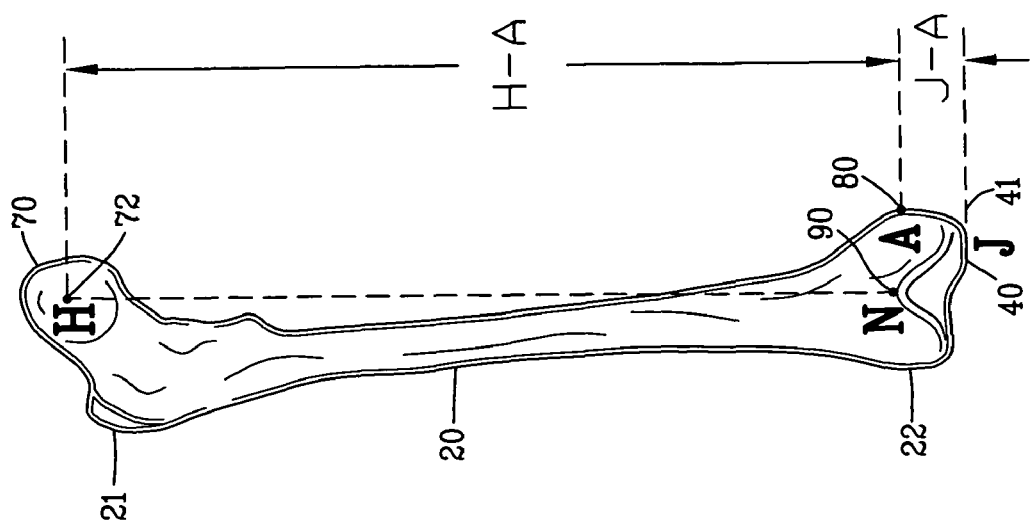
FIG. 9 is an enlarged view of femur bone of FIG. 2 illustrating the selection of three points on the femur bone.

FIG. 9 is an enlarged view of femur bone 20 of FIG. 2 illustrating the selection of three points on the femur bone 20. The first reference point (H) is the center 72 of the femoral head 70. The second reference point (A) is the adductor tubical 80 of the femur 20. Typically, the adductor tubercle 80 is preserved in almost every knee revision.

The distance between the first reference point (H) and the second reference point (A) is H-A. The original femorotibial joint location (J) 41 may be calculated through a relationship between the first reference point (H) and the second reference point (A) with the formula set forth above.

Figure 10:
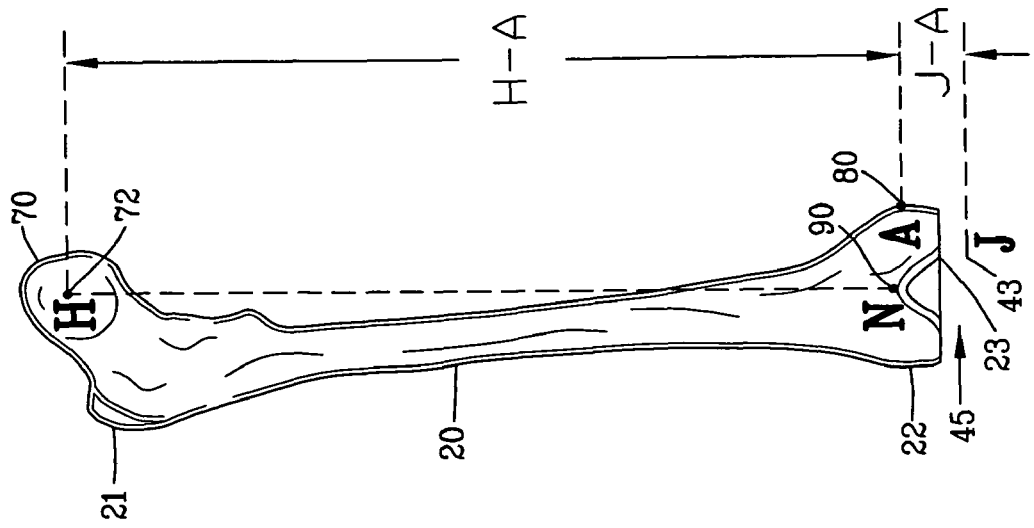
FIG. 10 is a view similar to FIG. 9 illustrating a femur bone having a severed distal end.

FIG. 10 is a view similar to FIG. 9 illustrating a femur bone 20 having a severed distal end 23. Although the distal end 22 of the femur 20 has been severed creating the gap 45, the method and apparatus of the present invention identifies a second implant femorotibial joint 43. A comparison of FIGS. 9 and 10 illustrates the location of the second implant femorotibial joint 43 of FIG. 10 is commensurate with the location of the original femorotibial joint location (J) 41.

Figure 11:
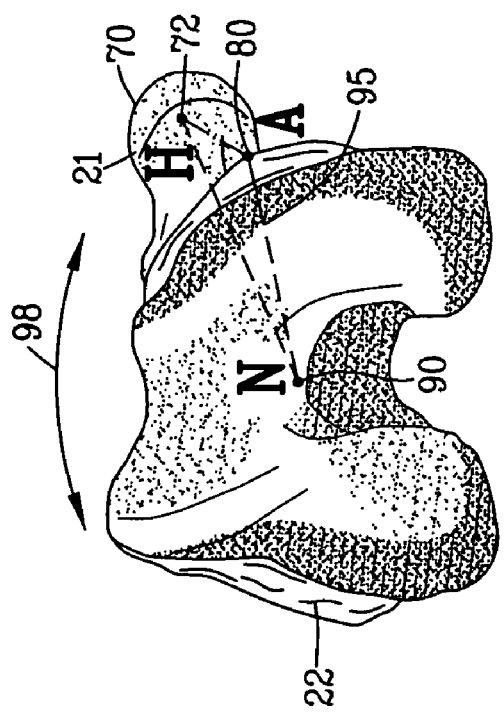
FIG. 11 is an enlarged bottom view of the distal end of the femur of FIG. 6.

FIG. 11 is an enlarged bottom view of the distal end 22 of the femur 20 of FIG. 6. A third reference point (N) is selected relative to a center of a notch 90 of the distal end 22 of the femur 20 of the patient 11. Preferably, the third reference point (N) is the center of the notch 80 of the distal end 22 of the femur 20. The third reference point (N) in combination with the first reference point (H) and the second reference point (A) define a femur reference plane 95. The femur reference plane 95 extends through the first reference point (H), the second reference point (A) and the third reference point (N). The femur reference plane 95 assists the surgeon in orientating the femur 20 in the correct rotational position as shown by the arrows 98.

Figure 12:
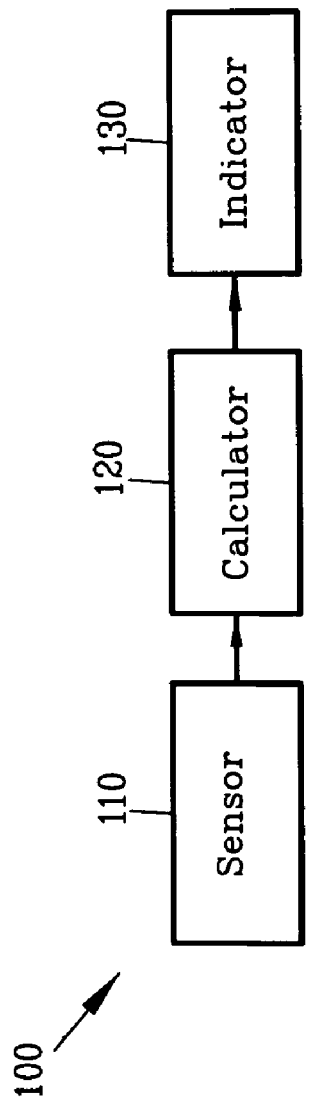
FIG. 12 is a block diagram of the apparatus of the present invention.

FIG. 12 is a block diagram of the apparatus 100 of the present invention for identifying the original femorotibial joint location 40 in a revision knee replacement of a patient 11. A sensor 110 senses the spatial relationship with the between the first reference point (H), second reference point (A) and the third reference point (N) of the patient 11.

A calculator 120 determines the location of the second implant femorotibial joint 43 shown in FIG. 10 of the patient 11 through a calculated distance between the first reference point (H) and the second reference point (A). The calculator 120 determines the orientation of the femur reference plane 95 shown in FIG. 11.

An indicator 130 indicates the position of the original femorotibial joint location 40. The indicator 130 indicates the femur reference plane 95 for assists the surgeon in orientating the femur 20 in the correct rotational position.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A method of identifying the original femorotibial joint location in a revision knee replacement of a patient, comprising the step of:
    removing an original prosthesis from the femur of the patient;
    selecting a first reference point (H) relative to the femoral head of the patient;
    selecting a second reference point (A) relative to the adductor tubical of the femur of the patient;
    determining the distance between the first reference point (H) and the second reference point (A);
    calculating the original femorotibial joint location (J) of the patient through a distance relationship between the first reference point (H) and the second reference point (A); and
    attaching a replacement prosthesis on the femur of the patient in accordance with the calculated original femorotibial joint location (J) of the patient.

2. A method of identifying the original femorotibial joint location in a revision knee replacement of a patient as set forth in claim 1, wherein the step of selecting the first reference point (H) relative to the femoral head of the patient includes selecting the center to the femoral head of the patient.

3. A method of identifying the original femorotibial joint location in a revision knee replacement of a patient as set forth in claim 1, wherein the step of selecting the second reference point (A) relative to the adductor tubical of the patient includes selecting the adductor tubical of the patient.

4. A method of identifying the original femorotibial joint location in a revision knee replacement of a patient as set forth in claim 1, wherein the step of calculating the original femorotibial joint location (J) includes calculating the original femorotibial joint location (J) through the formula: distance (J-A)/distance (H-A)=constant.

5. A method of identifying the original femorotibial joint location in a revision knee replacement of a patient as set forth in claim 1, wherein the step of calculating the original femorotibial joint location (J) includes calculating the original femorotibial joint location (J) through the formula: distance (J-A)/distance (H-A)=0.13.

6. A method of identifying the original femorotibial joint location in a revision knee replacement of a patient, comprising the step of:
    selecting a first reference point (H) on the femoral head of the patient;
    selecting a second reference point (A) on the adductor tubical of the femur of the patient;
    determining the distance between the first reference point (H) and the second reference point (A) of the femur of the patient;
    calculating the original femorotibial joint location (J) through the relationship of the distance (J-A) divided by the distance (H-A) is equal to a constant; and
    attaching a replacement prosthesis on the femur of the patient in accordance with the calculated original femorotibial joint location (J) of the patient.

7. A method of identifying the rotation of the femur in a revision knee replacement of a patient, comprising the steps of:
    selecting a first reference point (H) relative to the femoral head of the patient;
    selecting a second reference point (A) relative to the adductor tubical of the femur of the patient;
    selecting a third reference point (N) relative to a center of a notch of the distal end of the femur of the patient;

calculating a femur reference plane extending through the first reference point (H), the second reference point (A) and the third reference point (N) for indicating the correct rotation of the femur of the patient; and aligning the femur of the patient in accordance with the calculated femur reference plane of the femur of the patient.

8. A method of identifying the rotation of the femur in a revision knee replacement of a patient as set forth in claim 7, wherein the step of selecting the first reference point (H) relative to the femoral head of the patient includes selecting the center to the femoral head of the patient.

9. A method of identifying the rotation of the femur in a revision knee replacement of a patient as set forth in claim 7, wherein the step of selecting the second reference point (A) relative to the adductor tubical of the patient includes selecting the adductor tubical of the patient.

10. A method of identifying the rotation of the femur in a revision knee replacement of a patient as set forth in claim 7, wherein the step of selecting the third reference point (N) relative to the center of the notch of the distal end of the femur includes selecting the center of the notch of the distal end of the femur.

11. A method of identifying the original femorotibial joint location and the rotation of the femur in a revision knee replacement of a patient, comprising the steps of:

selecting a first reference point (H) relative to the femoral head of the patient;

selecting a second reference point (A) relative to the adductor tubical of the femur of the patient;

selecting a third reference point (N) relative to a center of a notch of the distal end of the femur of the patient;

determining the distance between the first reference point (H) and the second reference point (A) of the femur of the patient;

calculating the original femorotibial joint location (J) of the patient through a distance relationship between the first reference point (H) and the second reference point (A) of the femur of the patient; and calculating a femur reference plane extending through the first reference point (H), the second reference point (A) and the third reference point (N) for indicating the correct rotation of the femur of the patient;

aligning the femur of the patient in accordance with the calculated femur reference plane for correctly positioning the rotation of the femur of the patient; and, attaching a replacement prosthesis on the femur of the patient in accordance with the calculated original femorotibial joint location (J) of the patient.

12. An apparatus for identifying the original femorotibial joint location in a revision knee replacement of a patient, the patient having a femur defining a first reference point (H) relative to the femoral head and a second reference point (A) relative to the adductor tubical of the femur of the patient, comprising:

a sensor for sensing a spatial relationship with the between the first reference point (H) and second reference point (A) of the femur of the patient;

a calculator for determining the original femorotibial joint location (J) of the femur of the patient through a calculated distance between the first reference point (H) and the second reference point (A) of the femur of the patient; and an indicator for indicating the position of the original femorotibial joint location of the femur of the patient.

13. An apparatus for identifying the original femorotibial joint location in a revision knee replacement of a patient as set forth in claim 12, wherein said calculator determines the original femorotibial joint location (J) of the patient through the formula: distance (J-A)/distance (H-A)=constant.

14. An apparatus for identifying the original femorotibial joint location in a revision knee replacement of a patient as set forth in claim 12, wherein said calculator determines the original femorotibial joint location (J) of the patient through the formula: distance (J-A)/distance (H-A)=0.13.

15. An apparatus for identifying the original femorotibial joint location and the rotation of the femur in a revision knee replacement of a patient, the patient having a femur defining a first reference point (H) relative to the femoral head, a second reference point (A) relative to the adductor tubical of the femur, and a third reference point (N) relative to a center of a notch of the distal end of the femur of the patient, comprising:

a sensor for sensing a spatial relationship with the between the first reference point (H), the second reference point (A) and the third reference point (N) of the femur of the patient;

a calculator determining the original femorotibial joint location (J) of the femur of the patient through a calculated distance between the first reference point (H) and the second reference point (A) of the femur of the patient;

said calculator determining a femur reference plane extending through the first reference point (H), the second reference point (A) and the third reference point (N) of the femur of the patient; and an indicator for indicating the position of the original femorotibial joint location and the correct rotation of the femur of the patient.

* * * * *